(12) United States Patent
Daniel et al.

(10) Patent No.: US 11,754,561 B2
(45) Date of Patent: Sep. 12, 2023

(54) FUNCTIONALIZED BIOCHIPS FOR SPR-MS COUPLING

(71) Applicants: GENOPTICS, Orsay (FR); CENTRE NATIONAL DE LA RECHERCHE SCIENTIFIQUE, Paris (FR); UNIVERSITE D'EVRY VAL D'ESSONNE, Evry (FR)

(72) Inventors: Régis Daniel, Issy les Moulineaux (FR); Florence Gonnet, Villiers sur Orge (FR); William Buchmann, Sainte Genevieve des Bois (FR); Sophie Bellon, Paris (FR); Nathalie Jarroux, Ballainvilliers (FR); Marielle Anger-Leroy, Les Ulis (FR)

(73) Assignees: GENOPTICS, Orsay (FR); CENTRE NATIONAL DE LA RECHERCHE SCIENTIFIQUE, Paris (FR); UNIVERSITE D'EVRY VAL D'ESSONNE, Evry (FR)

(*) Notice: Subject to any disclaimer, the term of this patent is extended or adjusted under 35 U.S.C. 154(b) by 301 days.

(21) Appl. No.: 15/149,833

(22) Filed: May 9, 2016

(65) Prior Publication Data
US 2016/0377610 A1    Dec. 29, 2016

Related U.S. Application Data

(63) Continuation of application No. 12/734,854, filed as application No. PCT/FR2008/052149 on Nov. 27, 2008, now abandoned.

(30) Foreign Application Priority Data

Nov. 27, 2007 (FR) ...................... 0759351

(51) Int. Cl.
*G01N 33/543* (2006.01)
*G01N 21/552* (2014.01)
(Continued)

(52) U.S. Cl.
CPC ..... *G01N 33/54373* (2013.01); *G01N 21/554* (2013.01); *G01N 33/54353* (2013.01);
(Continued)

(58) Field of Classification Search
None
See application file for complete search history.

(56) References Cited

U.S. PATENT DOCUMENTS

2005/0260423 A1   11/2005   Natesan
2010/0285512 A1   11/2010   Daniel et al.

FOREIGN PATENT DOCUMENTS

| WO | WO 97/09608  | 3/1997 |
| WO | WO 03/005890 | 1/2003 |
| WO | WO 2006/073465 | 7/2006 |

OTHER PUBLICATIONS

Li, L. et al. Protein Adsorption on Oligo(ethylene glycol)-Terminated Alkanethiolate Self-Assembled Monolayers: The Molecular Basis for Nonfouling Behavior, J. Ohys. Chem. B vol. 109, pp. 2934-2941 (Year: 2005).*

(Continued)

*Primary Examiner* — Xiaoyun R Xu
(74) *Attorney, Agent, or Firm* — Nixon & Vanderhye, P.C.

(57) ABSTRACT

The invention relates to a method for coupling in-line the analysis of molecular interactions by surface plasmon resonance (SPR) with a structural identification by mass spectrometry using the same functionalized support for both types of analysis.

21 Claims, 11 Drawing Sheets

Specification includes a Sequence Listing.

(51) Int. Cl.
*G01N 33/553* (2006.01)
*G01N 33/68* (2006.01)

(52) U.S. Cl.
CPC ....... *G01N 33/553* (2013.01); *G01N 33/6851* (2013.01); *G01N 2560/00* (2013.01); *G01N 2570/00* (2013.01); *Y10T 436/24* (2015.01)

(56) References Cited

OTHER PUBLICATIONS

Patrie, S.M., et al. Self-Assembled Monolayers for MALDI-TOF Mass Spectrometry for Immunoassays of Human Protein Antigens, Analytical Chemistry, 79, 5878-5887 (Year: 2007).*
Nedelkov (Journal of Molecular Recognition J. Mol. Recognit. 2000).*
International Search Report for PCT/FR2008/052149, dated Jul. 3, 2009.
French-language Written Opinion of the International Searching Authority for PCT/FR2008/052149, dated Jul. 3, 2009.
Lu, H.B. et al., "Attachment of Functionalized Poly(ethylene glycol) Films to Gold Surfaces", Langmuir, vol. 16, No. 4, (Feb. 22, 2000), pp. 1711-1718. On-line Jan. 14, 2000.
Becker, C.F.W. et al., "Functional Immobilization of the Small GTPase Rab6A on DNA-Gold Nanoparticles by Using a Site-Specifically Attached Poly(ethylene glycol) Linker and Thiol Place-Exchange Reaction", Chembiochem, vol. 8, No. 1, (Jan. 2, 2007), pp. 32-36.
Mannelli, I. et al., "Bioadhesive nanoareas in antifouling matrix for highly efficient affinity sensors", Proceedings of SPIE—The International Society for Optical Engineering—Biosensing 2008, vol. 7035, (Aug. 29, 2008), pp. 70350Y-1-70350Y-10.
"How Does Surface Plasmon Resonance Work?", http://www.bionavis.com/technology/spr/.
Vanderah et al, "Self-Assembled Monolayers of Methyl 1-Thiahexa(ethylene oxide) for the Inhibition of Protein Adsorption", Langmuir, 2002, v. 18, pp. 4674-4680.
Xia et al, "Functionalized Poly(ethylene glycol)-Grafted Polysilosane Monolayers for Control of Protein Binding", Langmuir 2002, v. 18, pp. 3255-3262.

* cited by examiner

PEO-NHS biochip:

PEO-NHS-functionalized surface

PEO-NHS biochip:
Anti-β-lactoglobulin antibody spots

MUA-CDI biochip:

MUA-CDI biochip:
Anti-β-lactoglobulin antibody spots

Image taken at the end of injection of 200 µg/ml of ovalbumin

Injection of the proteins separately in increasing concentration:
1, 10, 100 and 200 ug/ml Image taken at the end of injection of 200 μg/ml of β-lactoglobulin PEO-functionalized gold Anti-ovalbumin 600 nM
~ 80pg/mm², i.e. 1.8fmol/mm²

Anti-β-lactoglobulin 600 nM
~ 33pg/mm², i.e. 1.8fmol/mm²

MS/MS spectrum of the ion m/z 1555.7

MS/MS spectrum of the ion m/z 1687.7 (ovalbumin)

MS/MS spectrum of the ion m/z 1773.9 (ovalbumin)

```
Ion m/z   Mass exp.  Mass calc.    ppm        Peptide
1555.7000  1554.6927  1554.7137   -13.47   K.AFKDEDTQAMPFR.V
1687.8000  1686.7927  1686.8325   -23.60   R.GGLEPINFQTAADQAR.E
1773.9000  1772.8927  1772.8918    0.55   K.ISQAVHAAHAEINEAGR.E
```

Protein identified by mascot: chicken ovalbumin score: 145
Sequence coverage: 11%

Sequence of chicken ovalbumin (SEQ ID No. 1) and peptides identified (underlined)

```
  1  MGSIGAASME  FCFDVFKELK  VHHANENIFY  CPIAIMSALA  MVYLGAKDST
 51  RTQINKVVRF  DKLPGFGDSI  EAQCGTSVNV  HSSLRDILNQ  ITKPNDVYSF
101  SLASRLYAEE  RYPILPEYLQ  CVKELYRGGL  EPINFQTAAD  QARELINSWV
151  ESQTNGIIRN  VLQPSSVDSQ  TAMVLVNAIV  FKGLWEKAFK  DEDTQAMPFR
201  VTEQESKPVQ  MMYQIGLFRV  ASMASEKMKI  LELPFASGTM  SMLVLLPDEV
251  SGLEQLESII  NFEKLTEWTS  SNVMEERKIK  VYLPRMKMEE  KYNLTSVLMA
301  MGITDVFSSS  ANLSGISSAE  SLKISQAVHA  AHAEINEAGR  EVVGSAEAGV
351  DAASVSEEFR  ADHPFLFCIK  HIATNAVLFF  GRCVSP
```

FIG. 6B

FUNCTIONALIZED BIOCHIPS FOR SPR-MS COUPLING

This application is a continuation of application Ser. No. 12/734,854 (pending), filed May 27, 2010 (published as US 2010-0285512 A1), which is the U.S. national phase of International Application No. PCT/FR2008/052149, filed 27 Nov. 2008, which designated the U.S. and claims priority to France Application No. 0759351, filed 27 Nov. 2007, the entire contents of each of which are hereby incorporated by reference.

The invention relates to a method for coupling in-line the analysis of molecular interactions by surface plasmon resonance (SPR) with a structural identification by mass spectrometry using the same functionalized support for both types of analysis.

With the development of proteomic sciences and in the extension of that of genomics, a very high demand has emerged for effective, high-throughput analytical technologies, in particular for searching for and identifying biomarkers. In addition, all the data currently produced by studying the genome, the proteome and the glycome reveal a scheme of cell function based on a complex network of dynamically interacting biomolecules. Many studies are carried out in an attempt to gain a better understanding of the various phenomena involved in the regulation of the proteome. However, there are few adequate technical solutions that make it possible to investigate this network. Recent advances in proteomics have been obtained by evolution of the existing technologies and by developing new approaches based on the coupling of separative techniques with mass spectrometry. Thus, the combination of 2D electrophoresis with mass spectrometry, and then the coupling of liquid chromatography (LC) with mass spectrometry, LC-MS and LC-MS-MS, for identifying and analyzing proteins, have emerged.

More recently, the use of biochips (lab-on-chip) has been developed for exploring the genome and the proteome. With regard to the study of the interactions between biomolecules, a new approach is found to be promising by coupling two analytical techniques—surface plasmon resonance (or SPR) and mass spectrometry (or MS), and more particularly MALDI mass spectrometry with the biochip in itself as sole interface. SPR makes it possible to quantify and analyze the interactions between biomolecules from the kinetic and thermodynamic point of view, whereas MS provides information on their molecular structures. Thus, the first results of this strategy called BIA/MS (for Biomolecular Interaction Analysis/Mass Spectrometry) were obtained in 1997 by the team of Randall W. Nelson. Since then, several teams have concentrated their efforts so as to facilitate SPR/MS coupling according to various strategies (Nedelkov, 2003).

The current main approach consists of the microelution of the molecules retained on the SPR chip by means of appropriate buffers. The material is then concentrated and its salts exchanged on resins, and optionally treated (derivatization, peptide digestion) before being analyzed by mass spectrometry. Although these microelution approaches enable the molecules retained in SPR to be recovered and then analyzed by mass spectrometry, they suffer a certain number of limitations, in particular the need, before the MS analysis, for several time-consuming and reactant-consuming steps (this is because the material recovered is often eluted in a denaturing buffer that is incompatible with MS and that needs to be exchanged with another buffer). These various steps can result in contaminations and also in a loss of material with, as a result, low yields and detection problems.

A second strategy, according to which the two analyses, SPR and MALDI-MS, are carried out on the same chip, is currently being explored. Most of these SPR-MS coupling studies have been carried out on Biacore instruments, the SPR analysis system currently most widely used. This Biacore system uses a closed chip configuration with an internal microfluidic circulation. For SPR-MS analysis, the chip, after SPR analysis, is extracted from the biosensor, washed and dried. Since it is located inside the biochip, the interaction zone is not directly accessible and it is therefore necessary to open the biochip. This procedure is irreversible and the Biacore chips are destroyed during the recovery of the interaction zone and cannot therefore be re-used for repeated SPR analyses (Nedelkov, *J. Mol. Recogn.* 2000, 13, 140-145). In addition, this system requires a step of post-SPR treatments comprising a washing phase in order to remove the detergents or buffers used during the SPR analysis, but also all the compounds present, in the fluidic system, that may cause a reduction in the signal in mass spectrometry. This rinsing step must be carried out with a solution that does not disrupt the receptor-analyte interaction. Furthermore, on the Biacore biochips, it is possible to immobilize only a limited number of receptors in microchannels inside these biochips (a maximum of 4 over a surface area of approximately 1 $mm^2$).

Faced with this situation, the considerable emergence of chips in the "microarray" format allowing the deposit of a large number of molecules at their surface means that an advantageous application in the field of SPR analysis can be foreseen. Thus, Nedelkov et al. (2006) have demonstrated the feasibility of performing coupling between SPR and MS in "microarray format", using a closed Biacore-type biochip in a plastic support (CM5) inside which 440 spots have been deposited. After SPR analysis in a Biacore apparatus, the chip was extracted from the SPR instrument and then washed and dried. The closed biochip was then cut up with a hot punch, designed to melt the plastic around the chip so as not to break it. The cut chip was subsequently placed, by means of a support, in a MALDI-TOF mass spectrometer. It is the first study of SPR-MS coupling described in the array format with the Biacore SPR technique. It is important to note that, with this device described by Nedelkov, only the MS analysis enables spatial resolution of the various spots placed on the chip. This is because the SPR instrument used for this experiment does not make it possible to differentiate the spots individually since the SPR signal is averaged over the entire surface area of the fluidics (i.e. over 1 $mm^2$). With this system, the spots of interest cannot therefore be identified, which does not allow a multiplex analysis.

In addition to the "microarray" format, a new imaging functionality has emerged which makes it possible to obtain an SPR analysis of multiplex type, i.e. on a multiplicity of samples analyzed simultaneously and in real time (*Surface plasmon microscopy*, B. Rothenhausler, W. Knoll, *Nature*, 1988, 332, 615-617).

The coupling of the SPR and MALDI-MS analytical techniques on the same biochip-type interface is dependent on the surface chemistry developed in order to functionalize the biochip. This chemistry must, on the one hand, allow optimum binding of the receptors and, on the other hand, be compatible with SPR analysis and MALDI-MS analysis. In this context, in 2002, Nedelkov proposed the use of self-assembled monolayers (SAMs) (*Proteomics* 2002, 2 441-446) using MUA (mercaptoundecanoic acid) alkanethiol chains known to form an organized monolayer on metal surfaces and particularly on gold. Recently, a SPRi-MS system in the microarray format has been presented, in which the biochip is functionalized with MUA alkanethiol chains (Nedelkov, *Analytical Chemistry* 2007, pp. A-D). However, this type of MUA self-assembled monolayer has the drawback of being responsible for nonspecific interactions due to the hydrophobic nature of the alkyl chains.

In this context, the inventors have developed the present invention, comprising the in-line coupling of SPR with mass spectrometry, in particular matrix-assisted laser desorption/ionization mass spectrometry (or MALDI-MS). Other desorption/ionization methods can be envisioned for in-line SPR-MS coupling taking place on the same surface and in the microarray format: DESI-MS (desorption electrospray ionization), FAB-MS (fast atom bombardment) or SIMS-MS (secondary ion mass spectrometry). These MS analysis techniques are more particularly used for analytes of low masses (<2000 Da), and have not to date made it possible to carry out the analysis of high-mass biomolecules such as proteins.

An object of the present invention is a method for fabricating a chip which may serve as a common support for SPR-MS coupled analysis.

An object of the invention is also a method for analyzing biomolecules which makes it possible to carry out the entire SPR-MS experiment, going from the analysis and quantification of the interactions by SPR, to the fine characterization by mass spectrometry, on the same support and in the "microarray format". The entire SPR-MS experiment can thus be carried out without the analyte being either moved or treated. This is because the analyte, the specific interaction of which with a receptor molecule immobilized on the biochip is detected by SPR, is directly analyzed by mass spectrometry without a microelution step. Thus, the analyte is protected against the action of denaturing buffers. Since it is directly analyzed on the biochip by mass spectrometry, the analyte does not undergo any extraction that would cause losses. The buffers used are compatible with both SPR and MS analyses.

The inventors have developed a method for functionalizing a solid support that can be used in SPR in such a way as to make it compatible with the coupling of two analytical techniques: SPR, in particular SPR imaging (or SPRi) and mass spectrometry (MS), in particular MALDI-MS.

The method according to the invention is a method for functionalizing the metal face of an analysis support (or chip) intended for SPR and MS analyses, the metal face being preferably gold in the present invention. The method comprises grafting a self-assembled monolayer of poly (ethylene oxide) (PEO) directly onto the metal face of said support. To this end, the PEO is directly brought into contact with the metal face to be functionalized, this functionalization being carried out by chemical grafting.

Advantageously, the support thus modified has qualities enabling the fine analysis of the interactions between molecules while at the same time enabling their structural analysis. The modified support makes it possible in particular to reduce as much as possible the nonspecific interactions of biomolecules with respect to the monolayer during study of the interactions of analytes with the immobilized receptors. The limitation of the nonspecific adsorption of the analytes is obtained through the choice of the nature of the self-assembled monolayer composed of ethylene oxide units. It also makes it possible to advantageously improve the SPR-MS coupling by improving the signal-to-noise ratio. The modified support also advantageously allows in situ proteolytic digestion after receptor-analyte interaction in SPR. This proteolytic digestion thus provides access to a fine proteomic analysis by MS.

The method according to the invention comprises the functionalization of a metal face of a chip intended for SPR and MS analyses. As is well known to those skilled in the art, the SPR experiments are carried out by attaching "receptor" molecules to the functionalized metal face of the support (or chip) comprising a metal face for recording the surface plasmon resonance phenomenon. Thus, in order to observe a surface plasmon resonance phenomenon, it is necessary to use a metal surface which may be made of silver, gold, platinum, aluminum or copper. Advantageously, the metal face of the support is made of gold, which is the metal most generally used in SPR by those skilled in the art.

The dimensions of the supports used in SPR and the method for assembling them are known to those skilled in the art. Thus, in one particular embodiment, the support is composed of a glass slide onto which the metal surface, preferably the gold surface, is deposited. The thickness of the metal surface may in particular be between 10 nm and 100 nm. Advantageously, a layer of chromium can be intercalated between the glass slide and the metal surface. This layer of chromium can have a thickness of between 1 nm and 5 nm, preferably between 1 and 2 nm.

According to the method of the present invention, the metal face of the SPR support is functionalized by chemically grafting poly(ethylene oxide) (PEO) directly onto said metal face. This method therefore comprises direct grafting of PEO, i.e. a strong interaction is established between the sulfur atom of the thiol group of the PEO and the metal face of the support without an intermediate molecule. These PEO molecules organize themselves into a monolayer by self-assembly. This configuration is represented in FIG. 1.

In the context of the present invention, the term "self-assembly" or "self-assembled" refers to the ability of PEO chains to organize themselves spontaneously with respect to one another in the space after grafting (*Surface Science Reports* 61 (2006) 445-463).

In the context of the present invention, the term "monolayer" covers chains forming a dense and ordered structure in the plane of the metal face. It is typically an ordered monomolecular layer encountered in the case of alkanethiols.

The grafting can be carried out by any means known to those skilled in the art. For example, the support comprising the metal face can be immersed directly in a solution containing the PEO to be grafted. Alternatively, the PEO solution can be deposited solely on the metal face of the support.

The solution containing the PEO comprises the PEO to be grafted, dissolved in an appropriate solvent which does not impede the reaction for self-assembly of the PEO on the metal face of the support. This solvent can in particular be absolute ethanol, water, dichloromethane or dimethyl sulfoxide. In one particularly preferred embodiment, the solvent used is absolute ethanol. The PEO concentration in the solution can typically be between 0.5 and 10 mM, preferably between 1 and 5 mM, and, particularly preferably, the PEO concentration is approximately 2.5 mM. The latter concentration makes it possible to achieve 100% grafting.

The grafting is carried out at a temperature preferably between 4° C. and 100° C., preferably between 10° C. and 70° C., even more preferably between 15° C. and 30° C. Advantageously, the grafting is carried out at ambient temperature, i.e. at 20° C. The pressure conditions can also be adjusted. Thus, the reaction can be carried out in particular at a pressure of between $10^{-5}$ and 2 atmospheres. Preferably, the grafting reaction is carried out at atmospheric pressure. The grafting time is at least one hour. Preferably, the grafting time is at least 6 hours. Longer reaction times can be envisioned, in particular at least 12 hours or at least 24 hours. It is understood that the support can be brought into contact with the PEO to be grafted for a period that can exceed several weeks. However, in practice, the grafting time will in general be less than 15 days, preferably less than 7 days.

Advantageously, the grafting reaction is carried out by immersing the support in a solution of PEO dissolved in absolute ethanol between 15° C. and 30° C., at a pressure of 0.5 to 2 atmospheres for at least 6 hours.

Preferably, the reaction is carried out in such a way as to obtain a degree of coverage of PEO on the metal face of the support of more than 70%, preferably than 80%, preferably than 90%, preferably than 95%. Even more preferably, the degree of coverage of the support is essentially 100%. This percentage corresponds to the percent inhibition of the conductivity of the metal face after coverage with PEO, relative to the conductivity measured before coverage.

Advantageously, the PEO used in the context of the present invention is a compound of formula (I)

$$A\text{-}(CH_2)_n\text{---}(O\text{---}CH_2\text{---}CH_2)_x\text{-}D \qquad (I)$$

in which:

n is equal to 1 or 2;

x is an integer between 5 and 16;

A is a group for anchoring the PEO onto the metal surface of the support by covalent bonding; and D is an optionally modified group for the binding of biomolecules.

In a particular embodiment of the functionalization method, n is equal to 2. In one preferred embodiment, x is equal to 8.

In z particularly advantageous embodiment of the functionalization method according to the invention, the PEO is a short-chain PEO, in particular a PEO in which n is equal to 2 and x is equal to 8, i.e. a compound of formula:

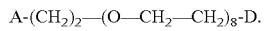

$$A\text{-}(CH_2)_2\text{---}(O\text{---}CH_2\text{---}CH_2)_8\text{-}D.$$

Group A is a group for anchoring the PEO molecule onto the metal surface of the support. Thus, if the metal surface is made of gold, silver, platinum or copper, A is a thiol group (—SH), known by those skilled in the art for grafting itself onto these metals, in particular onto gold, sulfur having a high affinity for gold. Thus, advantageously, one particular embodiment of the invention concerns a method as defined above, in which the metal of the metal face of the support is gold, and A is an —SH group.

In the context of the present invention, the "receptor" molecules are molecules of biological interest, in particular peptides, sugars or nucleic acids. In particular, the "receptor" molecules may be proteins, oligosaccharides or oligonucleotides.

Group D allows the binding of molecules to the functionalized support. The choice of the group D will therefore depend on the type of molecule to be immobilized, this choice being largely within the scope of those skilled in the art. Mention may be made of —COOH, —NH$_2$ and —CHO groups, inter alia, as group D. Group D may allow the direct binding of molecules, or indirect binding after modification of group D.

In the particular case where the receptor molecules are:

proteins, group D or modified group D may be an N-hydroxysuccinimide (NHS), succinimidyl ester or sulfosuccinimidyl ester group which will form amide bonds with the N-terminal primary amines of the proteins; a maleimide or iodoacetyl functionalized group, so as to react with thiolated proteins and result in a thioether bond;

oligosaccharides, group D or the group D modified by means of methods known to those skilled in the art, so as to react covalently with the reducing end of the sugar;

oligonucleotides (DNA or RNA), group D or modified group D may be a succinimidyl ester which will form an amide bond with the synthetic strand, itself functionalized at one of its ends with a primary amine function.

In a particularly preferred embodiment in the context of the immobilization of proteins, group D corresponds to a group that can be modified so as to give an N-hydroxysuccinimide (NHS) group, in particular the group —COOH.

In a particularly preferred embodiment of the functionalization method according to the invention, the PEO grafted onto the metal face of the support is a PEO of formula HS—CH$_2$—CH$_2$—(O—CH$_2$—CH$_2$)$_8$—COOH.

The PEO to be grafted is commercially available, in particular the PEO of formula HS—CH$_2$—CH$_2$—(O—CH$_2$—CH$_2$)$_8$—COOH, also known as O-(2-mercaptoethyl)-O'-(2-carboxyethy)heptaethylene glycol. Alternatively, the PEO to be grafted can be synthesized according to methods which are all in the scope of those skilled in the art (*J. Am. Chem. Soc.* 1993, 115, 10714-10721).

In a particular embodiment, the functionalization method according to the invention comprises:

1) prior cleaning of the support;

2) grafting of the PEO onto the cleaned support and self-assembly in a monolayer on the metal face of the support, as described above;

3) optionally, modification of group D of the PEO.

Above cleaning step 1) is carried out by any suitable means known to those skilled in the art. Specifically, cleaning may in particular be carried out by UV-ozone treatment of the metal surface to be functionalized. Alternatively, the support can be cleaned with sulfochromic acid.

After step 2) of grafting the PEO onto the support, the functionalized support can be stored preferably under dry conditions and/or preferably under cold conditions (approximately 4° C.), such as in a refrigerator (in particular in a contained atmosphere), before subsequent treatment or before use thereof for the analysis by SPR and/or MS.

Step 3), which is optional, corresponds to the modification of group D of the PEO. The need for a modification will depend on the type of group D at the end of the PEO grafted onto the metal face, as is well known to those skilled in the art. For example, if D represents a —COOH group, the latter can be modified so as to give an N-hydroxysuccinimide (NHS) group, under standard conditions known for this type of reaction. The NHS group used for the modification at the end of the PEO is well known for its reactivity as a protein-coupling agent (*Macromolecules* 35 (2002) 581-584).

After step 3 of optional modification of group D of the PEO, the functionalized support can be stored (preferably under dry conditions), in particular in a refrigerator (in particular in a contained atmosphere), before use in an analysis by SPR, optionally followed by an analysis by MS.

The invention also relates to the use of a PEO of formula (I) as defined above, according to all the variants envisioned, for functionalizing the metal face of a SPR analysis support.

The invention also relates to a functionalized SPR analysis support, comprising a metal face onto which a PEO as defined above is grafted. In this respect, the functionalized support according to the invention is in particular a functionalized support obtained according to the method described above. It may also comprise the "receptor" molecules immobilized on the functionalized support via a bond by means of the self-assembled monolayer of poly(ethylene oxide), in particular of group D or of modified group D of PEO, in particular functionalized with an NHS group. Thus, the support comprises "receptor" molecules in the form of a network of spots. This network of spots has the advantage of allowing the specific analysis of the interactions of a given "receptor" molecule with a sample of analytes, in particular in the context of a SPR or MS experiment.

The invention also relates to the use of a functionalized support as described above, in an analysis by SPR, in particular in an analysis by SPRi. In this context, "receptor" molecules are immobilized on the functionalized support via a bond by means of group D or of modified group D, in particular functionalized with an NHS group.

The protocol for immobilizing the "receptor" molecules depends on the type of group D of the PEO grafted onto the support and on the type of "receptor" molecules to be immobilized, as is well known to those skilled in the art.

Among the receptor molecules, mention may in particular be made of proteins (antigens, antibodies, peptides), nucleic acids (DNA, RNA oligonucleotides) and carbohydrates (oligosaccharides). These various types of molecules can be immobilized on the support through the appropriate choice of group D of the PEO grafted onto the support.

In the particular embodiment where group D is modified so as to give an NHS group or an NHS derivative, it is necessary to carry out a step of inactivation of the NHS groups that are not reacted at the end of the "receptor"-molecule immobilization step. A solution of lysine can in particular be used for this purpose. The lysine is present in this solution at a concentration of between 10 $\mu$M and 1 mM.

Advantageously, the "receptor" molecules are immobilized on the functionalized support described above in order to carry out an SPRi analysis. Compared with conventional SPR analysis, SPRi analysis provides access to the multiplex format, i.e. the simultaneous, real-time analysis (detection, quantification, visualization), without labeling, of a large number of samples. To do this, the "receptor" molecules are immobilized at the surface of the functionalized support in the form of a network of spots, the composition of which in terms of immobilized molecules is known and ordered. This network opens the door to spatial resolution in SPR, i.e. the spots of interest are visualized by SPR through imaging.

This spatial resolution will be conserved during the MALDI-MS analysis. Each spot may be interrogated individually by the MS analyzer, and thus each analyte specifically retained on the support may be identified by MS.

In order to carry out the analysis by SPR, in particular by SPRi, the functionalized support on which receptor molecules have been immobilized is placed in an SPRi or conventional SPR analyzer. The SPR or SPRi data are then acquired and used.

The major advantage of the functionalized support according to the present invention is that it allows simple and improved coupling between a SPR analysis and a MS analysis and it minimizes interferences due to nonspecific bindings on the surface, in particular observed during the use of other support functionalized with MUA described above. Indeed, after SPR, and advantageously SPRi, analysis, the functionalized support on which the "receptor" molecules are immobilized is removed from the SPR, or SPRi, analyzer and is placed directly (without intermediate steps) in a MALDI-MS mass spectrometer, with no destruction of the functionalized support and with neither microelution nor any changing of buffer solution of the analytes specifically retained during the SPR analysis. This is particularly advantageous since the solvents conventionally used for eluting molecules attached to the SPR support are not compatible with MS and therefore require an additional step of buffer exchange. This additional step takes time and can lead to contaminations and a loss of material.

Thus, the functionalized support according to the invention makes it possible to set up a simplified SPR-MS coupling, with improved yields. The invention therefore also relates to the use of a modified support as described above, for carrying out the analysis of the molecular interactions of a sample placed on the support, by surface plasmon resonance coupled with the structural analysis of said sample placed on the same support, by mass spectrometry, preferably by MALDI mass spectrometry.

In other words, the invention also relates to the use of a functionalized support as described above, for carrying out two consecutive analyses: an analysis by SPR and then an analysis by mass spectrometry.

The invention also relates to the use of a functionalized support as defined above, in a mass spectrometry experiment, in particular of MALDI type, in particular of MALDI-TOF type.

In the case of an analysis by MALDI spectrometry, those skilled in the art are aware that the samples present on the support should be coated in a suitable matrix (Hillenkamp, F.; Karas, M.; Beavis, R. C.; Chait, B. T. *Analytical Chemistry* 1991, 63, A1193-A1202).

Those skilled in the art may use the support according to the invention in a protein analysis of the analytes retained on the "receptor" molecules immobilized on the functionalized support, in particular by carrying out a step of in situ localized enzyme digestion directly on the surface, which will make it possible to obtain either the peptide fingerprint of a protein by MALDI-MS, or its sequence by MALDI-MS/MS.

The invention relates more particularly to a method for coupling an analysis by SPR, in particular SPRi, with an analysis by MS, in particular MALDI, comprising:

1) immobilizing one or more "receptor" molecules on a functionalized support according to the invention; then 2) placing the support in an SPR analyzer and analyzing, by SPR, the interactions between the "receptor" molecule(s) immobilized and a sample of analytes; then 3) removing the support from the SPR analyzer and placing it in a mass spectrometer, and structurally analyzing, by MS, the analytes specifically retained by the "receptor" molecules during the SPR analysis.

The MS will allow to structurally identify the analytes which have been specifically retained by the receptor molecules, themselves covalently bonded to the functionalized support according to the invention.

In the context of the present invention, the term "analyte" denotes chemical substances or compounds subjected to an analytical procedure so as to detect the presence thereof and/or measure a characteristic thereof (for example: content, concentration). They are in particular chemical substances or compounds of which it is desired to determine the capacity to interact with the "receptor" molecules immobilized on a support as described above. The analytes may correspond to a mixture, the content of which is unknown, for example a protein, carbohydrate, nucleic acid, etc., extract. The mixture could also contain a mixture of known proteins, carbohydrates, nucleic acids, etc.

During immobilization step 1), one or more "receptor" molecules can be immobilized. In this respect, several tens, several hundred, or even several thousand, different "receptor" molecules can be immobilized. Advantageously, the "receptor" molecules are immobilized in a discrete and ordered manner on the support of the invention in the form of spots. Thus, the position of each of these "receptor" molecules can be addressed directly, making it possible for the SPR and MS analyses to be carried out individually, spot-by-spot (i.e. "receptor"-molecule-by-"receptor" molecule). Thus, the functionalized support advantageously allows multiplexing during the MS analysis which follows the SPR analysis.

In one particularly preferred embodiment of the invention, the MS analyses are carried out by MALDI-MS. In this context, a matrix compatible with the MALDI analysis is deposited on the support before it is introduced into the mass spectrometer.

The inventors of the present method have thus been able to demonstrate that the functionalized support according to the invention makes it possible to carry out a localized enzyme digestion on each of the spots corresponding to an immobilized "receptor" molecule. Thus, the enzyme chosen can be deposited directly on the spots. Equipped with this additional functionality, the method of in-line SPRi-MS coupling described in the present invention offers the user the choice of two types of MS analysis on the functionalized support: one without enzyme digestion, resulting in determination of the whole mass of the analytes having been specifically retained on the receptors, and the other including an in situ enzyme treatment of the analytes retained (proteins, carbohydrates, nucleic acids), and giving more detailed structural data.

Thus, the invention also relates to a method for coupling an analysis by SPR, in particular SPRi, with an analysis by MS, in particular MALDI-MS, or MS/MS, comprising:
1) immobilization of one or more "receptor" molecules on a functionalized support according to the invention; then
2) placing the support in an SPR analyzer and analysis, by SPR, of the interactions between the "receptor" molecule(s) immobilized and a sample of analytes;
3) in situ localized enzyme digestion of the analytes retained on the spots of the "receptor" molecules immobilized on the functionalized support, then placing the support in a mass spectrometer, and structural analysis, by MS or MS/MS, of the products of digestion of the analyte(s) present on the functionalized support.

For example, in the case of a protein analysis, proteolysis directly on the surface will make it possible to obtain either the peptide fingerprint of a protein by MALDI-MS or its sequence by MALDI-MS/MS. Equipped with this functionality, the method of in-line SPRi-MS coupling described in the present invention thus opens the door to fine structural analysis, in particular in the case of proteomic analyses.

In addition, these two analyses can be successively combined, on the same functionalized support according to the following sequence: SPR analysis and capture of the analyte, characterization of the whole mass of the analyte by MS, followed by enzyme digestion of the analyte and by a second analysis by MS. This is because, subsequent to the in-line SPRi/MALDI-MS coupling providing access to the whole mass of the analyte, the authors have been able to demonstrate that it is possible to remove the matrix necessary for the characterization by MALDI-MS, in order to carry out an enzyme digestion of the molecules bound to the support in situ. The removal of the matrix is carried out by rinsing with the matrix-solubilizing solution, which, for this use, is free of acid. A solubilizing solution of the acetonitrile or ethanol type may in particular be used.

In this case, the invention relates to a method for coupling an analysis by SPR, in particular SPRi, with an analysis by MS, in particular MALDI-MS, comprising:
1) immobilization of one or more "receptor" molecules on a functionalized support according to the invention; then
2) placing the support in an SPR analyzer and analysis, by SPR, of the interactions between the "receptor" molecule(s) immobilized and a sample of analytes; then
3) removal of the support from the SPR analyzer and placing said support in a mass spectrometer, and structural analysis, by MS, of the analytes specifically retained by the "receptor" molecules during the SPR analysis; then
4) in situ localized enzyme digestion of the analytes retained on the spots of the "receptor" molecules immobilized on the functionalized support, coating of the samples in a matrix suitable for an analysis by MALDI-MS, placing the support in a mass spectrometer, and structural analysis, by MALDI-MS or MALDI-MS/MS, of the products of digestion of the molecule(s) present on the functionalized support.

In one particular embodiment, the structural analysis of above step 3) is carried out by MALDI-MS. In this case, after this analysis, the matrix used for the MALDI-MS is removed before step 4.

DESCRIPTION OF THE FIGURES

FIGS. 2A-2D represent the results of the comparison between PEO-NHS self-assembled monolayers and MUA-CDI self-assembled monolayers grafted to the gold surface of SPR-MS biochips.

FIG. 6B shows sequence of chicken ovalbumin and peptides identified.

EXAMPLES

Example 1

Protocol for Preparing a PEO-NHS Self-Assembled Monolayer Slide

Dimensions of the Detachable Biochip

Glass slide 500 µm thick, with dimensions of 12 mm×28 mm.

Thickness of chromium: 1 to 2 nm.

Thickness of the gold layer deposited at the surface: 50 nm.

Characteristics of the PEO

The bifunctionalized PEO used is of commercial origin (Sigma-Aldrich; ref: 672688). It is O-(2-mercaptoethyl)-O'-(2-carboxyethy)heptaethylene glycol, composed of 8 EO [ethylene oxide] units and functionalized at its two ends:

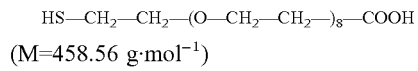

($M=458.56$ g·mol$^{-1}$)

The thiol (mercapto) function allows anchoring of the polymer onto the metal face of the glass slide. The carboxylic acid function at the other end allows the functionalization of the chain, necessary for the covalent bonding of the "receptor" biomolecules.

Figure 1:
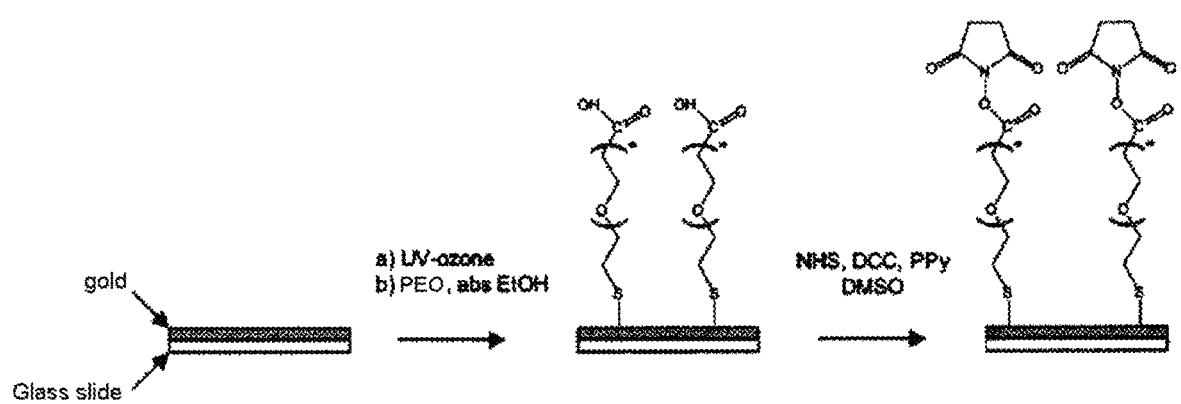
FIG. 1 is a diagram representing a support according to the invention, comprising a metal face made of gold and the steps for functionalizing this surface. The surface is functionalized with a PEO of formula HS—$CH_2$—$CH_2$—(O—$CH_2$—$CH_2$)$_8$—COOH, then this PEO is modified with an NHS group.

Protocol for Preparing the Deposit of PEO-NHS in the Form of a Self-Assembled Monolayer at the Surface of the Biochip After a prior cleaning step, the PEO is first deposited so as to form a self-assembled monolayer, and then, in the next step, its carboxyl end is functionalized with the N-hydroxysuccinimide group (cf. diagram FIG. 1).

1) Cleaning of the Slides by UV-Ozone Treatment

Gold-coated glass slides, the dimensions of which are given above, are placed on optical paper, gold face upward, and a UV-ozone treatment is carried out for 1 h.

2) Deposition of PEO: Protocol for a Slide

In a 100 ml beaker, 3 mg ($6.54\times10^{-6}$ mol) of HS—CH$_2$—CH$_2$—(O—CH$_2$—CH$_2$—)$_8$—COOH are dissolved in 2.6 ml of absolute ethanol (final PEO concentration of 2.5 mM or 1.15 mg/ml). The solution is homogenized in the beaker, and then a slide is immersed in said beaker, directly after the UV-ozone treatment.

The beaker is then covered with 3 layers of parafilm so as to prevent evaporation. The beaker is subsequently agitated for 6 hours (Rocking Platform speed=20). After this step, the PEO-treated slide is recovered and the excess solution is absorbed on blotting paper. The treated slide is then rinsed in two baths of absolute ethanol, dried, and then stored in a refrigerator while waiting to carry out the functionalization reaction with N-hydroxysuccinimide (NHS).

3) Functionalization of the PEO with N-hydroxysuccinimide

A solution of 1.09 ml of DMSO containing 27.6 mg ($2.4\times10^{-4}$ mol) of N-hydroxysuccinimide, 53 mg ($2.6\times10^{-4}$ mol) of N,N'-dicyclohexylcarbodiimide and 3.5 mg ($0.23\times10^{-4}$ mol) of 4-pyrrolidinopyridine is prepared in a 100 ml beaker. The solution is then homogenized.

The slide previously treated with the PEO is then placed in the freshly prepared solution of DMSO, and the beaker is covered with two layers of parafilm. The reaction is then carried out by leaving the solution to act for 24 hours with agitation (Rocking Platform speed=20). The excess solution is removed on blotting paper and the slide is then rinsed once in a bath of DMSO and then 5 times in baths of ultrapure water and once in a bath of absolute ethanol. The slide thus treated is then dried and then stored in a refrigerator, under dry conditions, before use.

Example 2

Figure 3A:
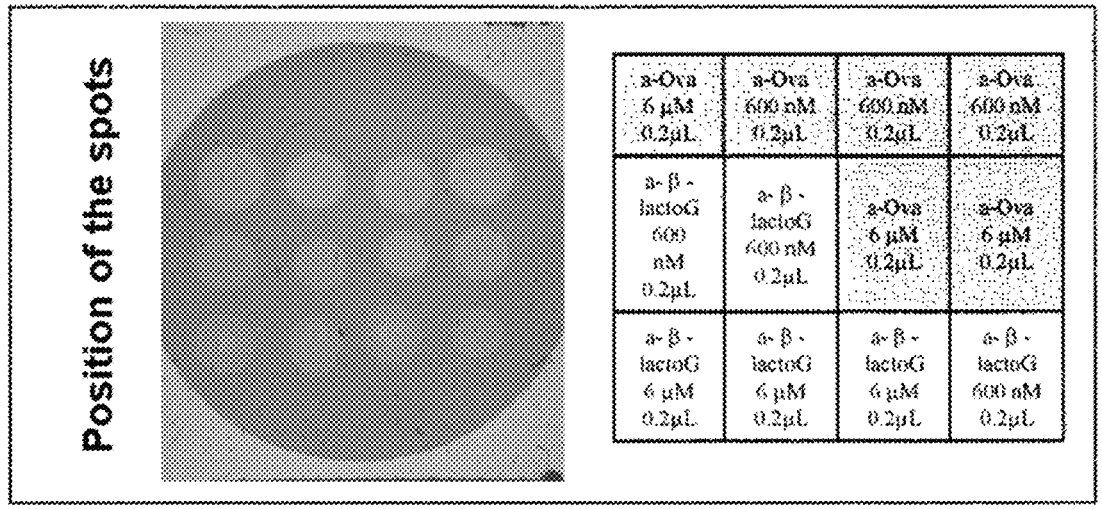
FIG. 3A shows successive injections of proteins, β-lactoglobulin then ovalbumin 1, 10, 100, 200 μg/ml, representing an SPRi experiment on a biochip having undergone a PEO-NHS surface treatment according to the invention.
Figure 3A:
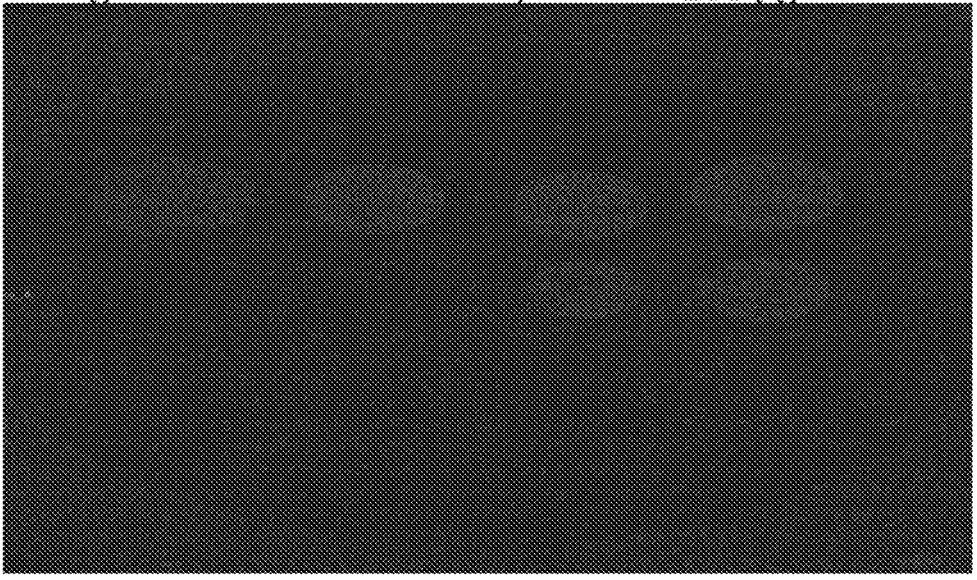
Figure 3B:
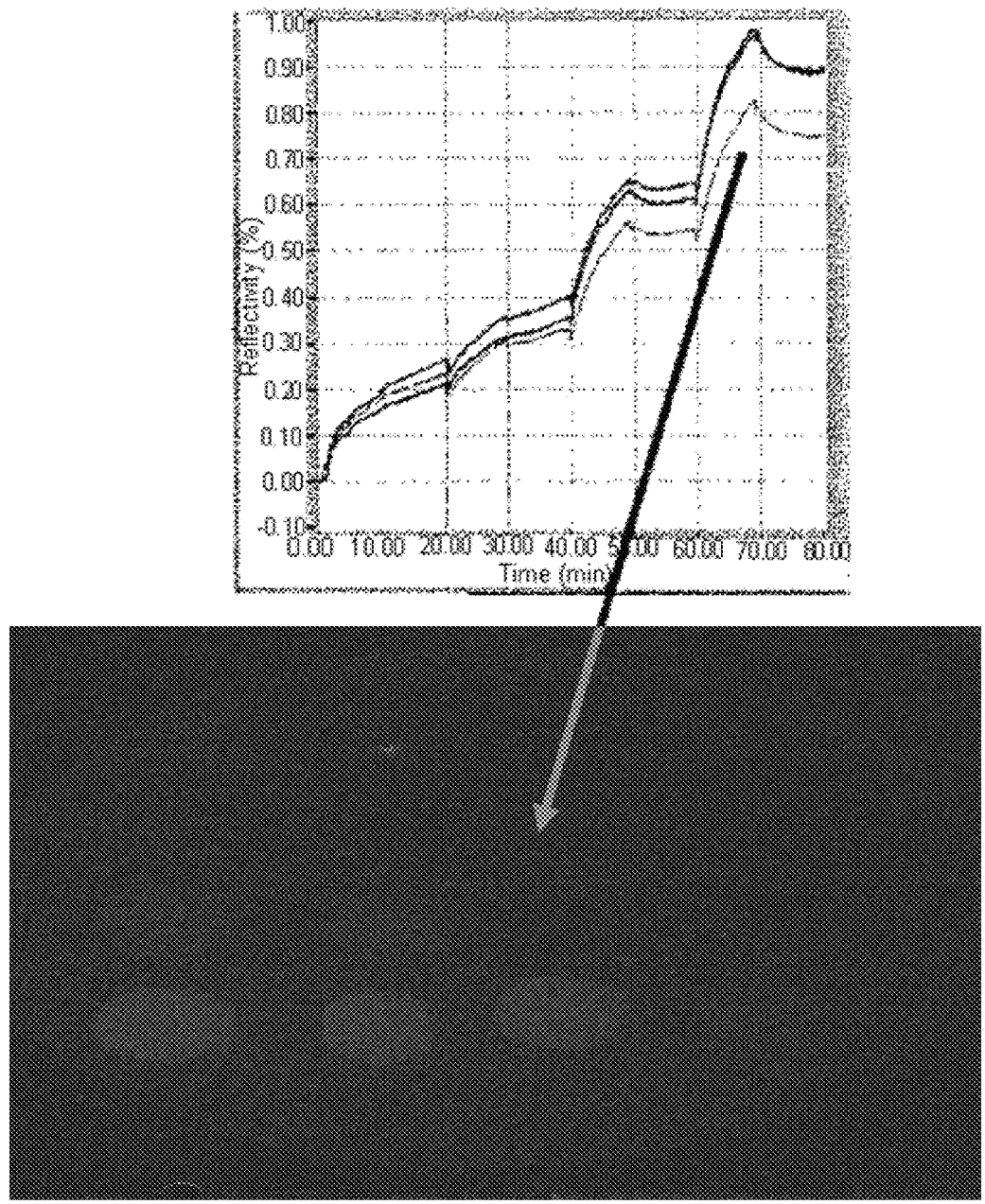
FIG. 3B shows successive injections of proteins, β-lactoglobulin then ovalbumin 1, 10, 100, 200 μg/ml and with FIG. 3A showing the specificity of interaction of the analytes for their receptors.
Figure 4A:
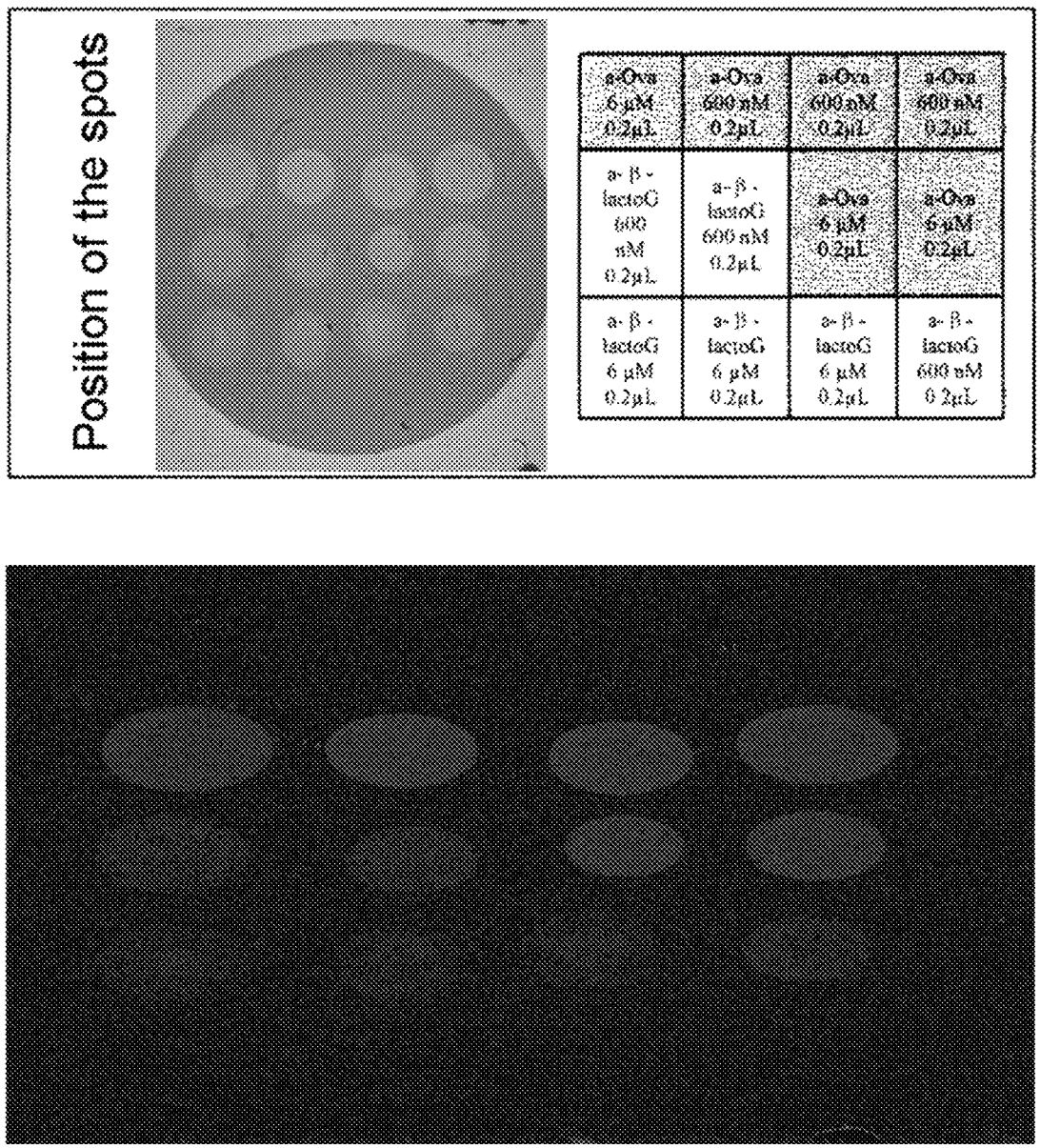
FIG. 4A, with FIGS. 4B and 4C represents an example of SPRi-MALDI-TOF MS coupling on a biochip of the type self-assembled PEO-NHS monolayer on a gold surface.
Figure 4B:
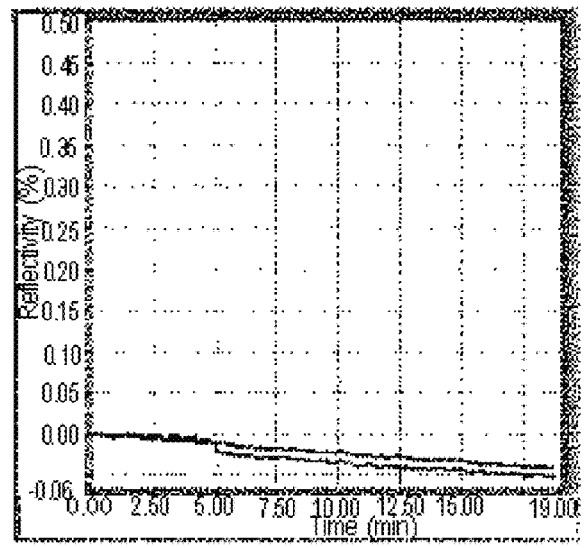
FIG. 4B shows results of PEO-functionalized gold, Anti-ovalbumin and Anti-β-lactoglobulin.
Figure 4B:
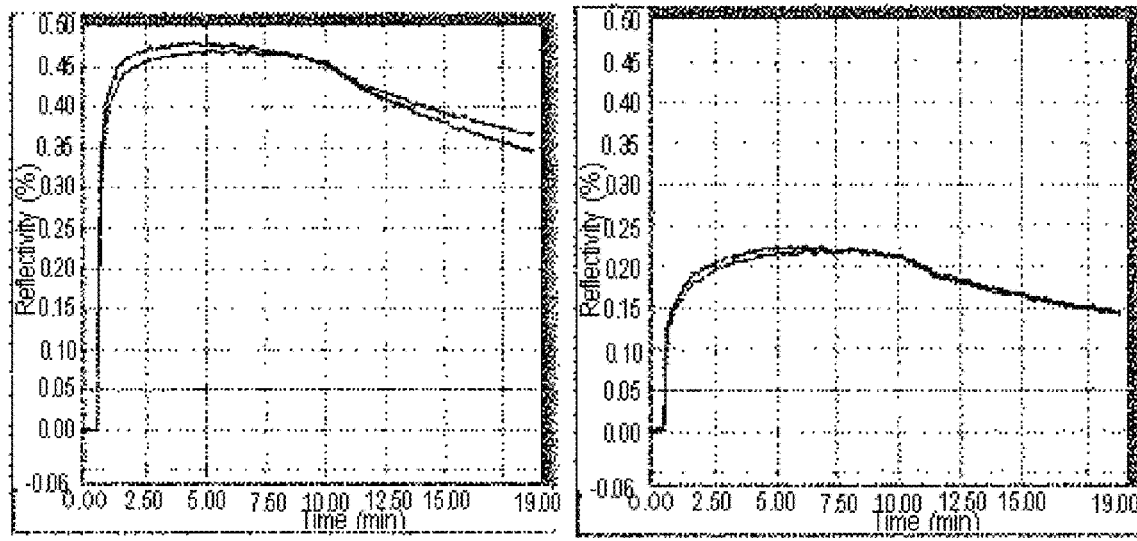
Figure 4C:
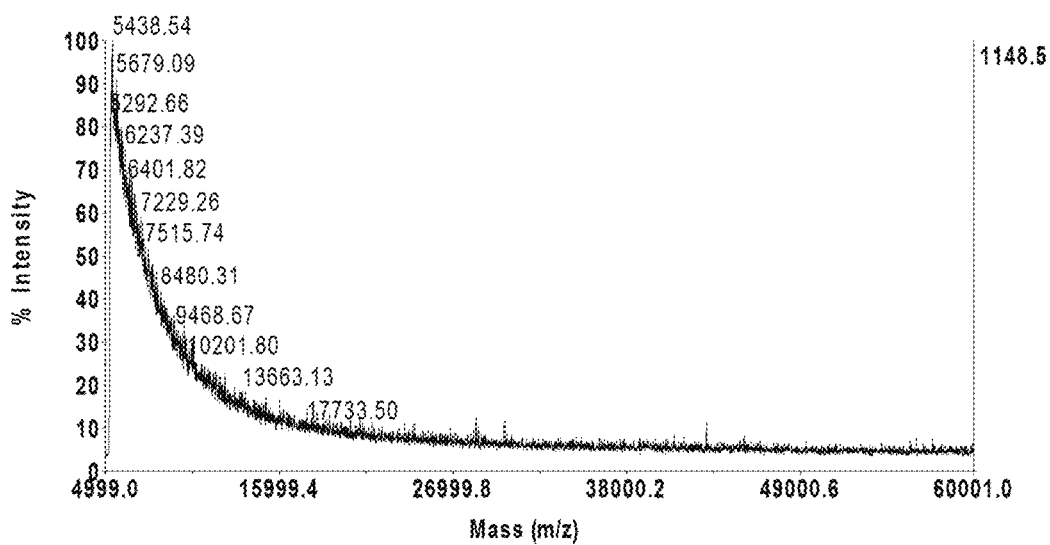
FIG. 4C shows an example of SPRi-MALDI-TOF MS of the example.
Figure 4C:
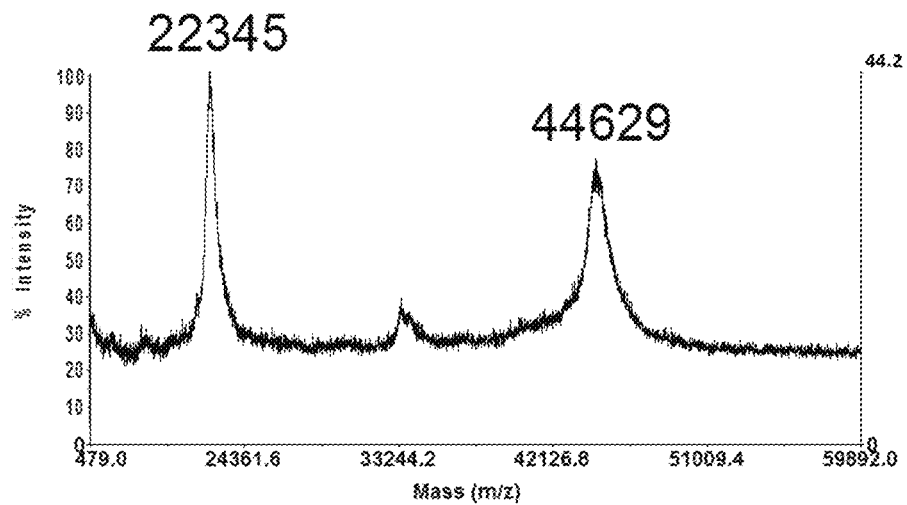
Figure 4C:
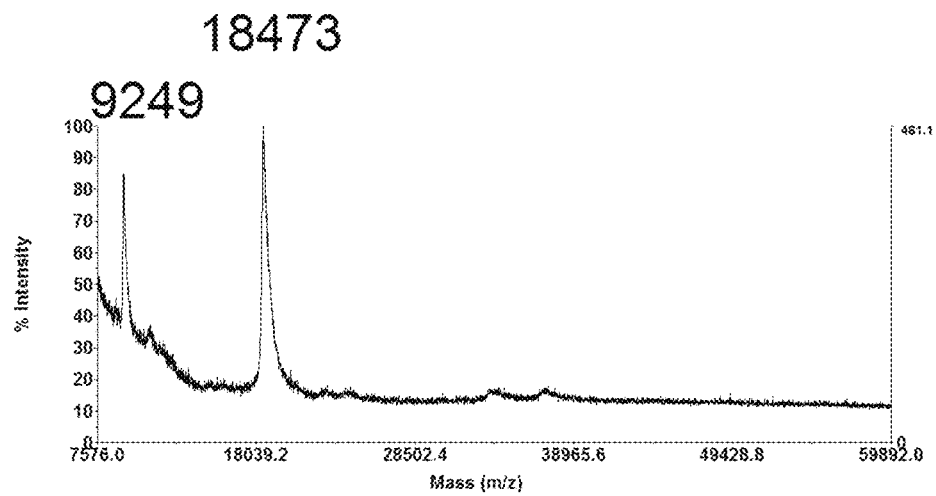

Presentation of an SPRi Experiment on a Biochip of the Type PEO-NHS Self-Assembled Monolayer at the Gold Surface This example relates to an SPRi experiment on a biochip having undergone a PEO-NHS surface treatment according to the invention and showing the specificity of interaction of the analytes for their receptors (cf. FIG. 3).

This experiment relates to the capacity for adsorption of two protein analytes, ovalbumin and β-lactoglobulin, onto spots of anti-ovalbumin and anti-β-lactoglobulin antibodies (600 nM and 6 µM) immobilized on the functionalized surface, in comparison with measurements carried out on zones without antibodies (zones corresponding to the PEO-NHS chemistry without antibodies) and where no adsorption of analytes is recorded.

The conditions of the experiment are the following:

The interaction of ovalbumin and of β-lactoglobulin with the anti-ovalbumin and anti-β-lactoglobulin antibodies immobilized on the surface is monitored by SPRi. At the beginning of the experiment, lysine (100 L M) is injected in order to neutralize the NHS groups of the PEO-functionalized surface which have not reacted with the antibodies. Next, the two proteins, ovalbumin and β-lactoglobulin (50 µg/ml), are successively injected at the flow rate of 50 µl/min. Solutions of increasing concentration of β-lactoglobulin (1, 10, 100 and 200 µg/ml) and then of increasing concentration of ovalbumin (1, 10, 100 and 200 µg/ml) are injected. The running buffer is 10 mM ammonium acetate, pH 7.5. The images shown illustrate the adsorption of the proteins onto their respective antibodies for concentrations of 200 µg/ml. No protein is adsorbed onto the lysine-inactivated, PEO-NHS-functionalized surface.

Example 3

Presentation of an SPRi-MALDI-TOF MS Coupling on a Biochip of the Type PEO-NHS Self-Assembled Monolayer on the Gold Surface This example relates to SPRi-MALDI-TOF MS coupling on a biochip having undergone a surface treatment according to the invention (cf. FIG. 4).

This example relates to the SPR analysis of the interaction of ovalbumin and of β-lactoglobulin with their respective anti-ovalbumin and anti-β-lactoglobulin antibodies (600 nM and 6 μM) immobilized on the functionalized surface in the form of spots, and to the detection of the protein analytes by MALDI-TOF MS.

The conditions of the experiment are the following. The interaction of the ovalbumin and of the β-lactoglobulin with the anti-ovalbumin and anti-β-lactoglobulin antibodies immobilized on the surface is monitored by SPRi. At the beginning of the experiment, lysine (100 μM) is injected in order to neutralize the NHS groups of the PEO-functionalized surface which have not reacted with the antibodies. Next, a mixture of the two proteins, ovalbumin and β-lactoglobulin (50 μg/ml), is injected at the flow rate of 50 μl/min. The beginning of the injection of the mixture of the two proteins corresponds to the time t=0. Next, the functionalized support is rinsed for 10 min (t=9 min to t=19 min) with the 10 mM ammonium acetate running buffer, pH 7.5. After the interaction data have been recorded by SPRi, the biochip is removed from the SPR instrument and then dried.

The image shown in FIG. 4 illustrates the adsorption of the proteins onto their respective antibodies after 9 minutes of injection. The MALDI-TOF mass spectra are carried out in positive linear mode (100 repeated shots and 500 accumulations; acceleration voltage 25 kV; voltage applied to the grid 93%; extraction delay 450 ns; laser intensity 2800). The chosen MALDI matrix is HABA [2-(4-hydroxyphenylazo) benzoic acid], at $10^{-1}$M in 50/50 water/acetonitrile 0.1% TFA. The matrix is deposited on the spots of antibodies and also on a zone of gold functionalized with PEO-NHS-Lys but without antibodies.

No interaction is detected on the support functionalized with PEO-NHS and neutralized with lysine. The anti-ovalbumin and anti-β-lactoglobulin antibodies present in the example specifically retained 1.8 fmol/mm$^2$ of protein. The MALDI-TOF mass spectra obtained in this example show a peak corresponding to a mono-charged ion attributed, according to its mass, to the protein specifically retained on its antibody.

Example 4

Comparison of Types of PEO-NHS Vs MUA-CDI Self-Assembled Monolayers Grafted to the Gold Surface of SPR-MS Biochips This example relates to the comparison between the PEO self-assembled monolayer surface chemistry according to the invention and the surface chemistry described more commonly in the literature in SPR, i.e. functionalization with MUA.

This comparison relates to the capacity for adsorption of β-lactoglobulin onto spots of anti-β-lactoglobulin antibodies placed on the two types of functionalized surface, and also to the level of nonspecific adsorption measured by SPRi on antibody-free zones.

The conditions of the experiment are the following. The interaction of the β-lactoglobulin with the anti-β-lactoglobulin antibody (6 μM) immobilized on the two types of surface is monitored by SPR. At the beginning of the experiment, lysine (100 μM) is injected in order to neutralize the NHS and CDI (carbonyldiimidazole) groups of the surfaces functionalized with PEO and MUA, respectively, which have not reacted with the antibodies. Next, a solution of β-lactoglobulin (50 μg/ml) was injected at the flow rate of 50 μl/min. The beginning of the β-lactoglobulin injection corresponds to the time t=0. The functionalized supports are then rinsed for 5 min (t=9 min to t=14 min) with the 10 mM ammonium acetate running buffer, pH 7.5.

The results are represented in FIG. 2.

It is noted that the zone functionalized with MUA-CDI (FIG. 2C, no antibodies) retains proteins nonspecifically, despite rinsing for 5 minutes. This nonspecific adsorption should therefore be taken into account in the quantification of proteins specifically adsorbed onto the antibody (FIG. 2D). In addition, this nonspecific adsorption may be a source of difficulty during the identification, by mass spectrometry, of the proteins specifically retained on the probes.

Figure 2A:
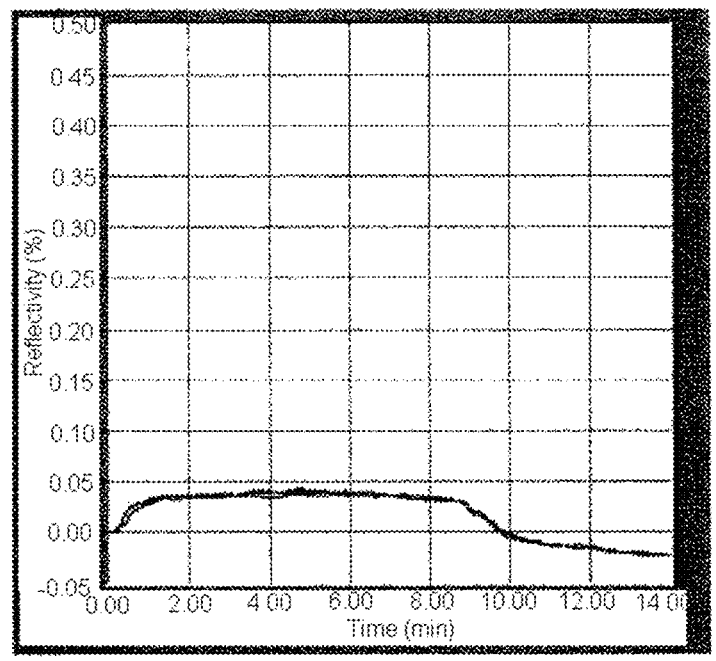
FIG. 2A provides results of PEO-NHS biochip with a PEO-NHS-functionalized surface.
Figure 2B:
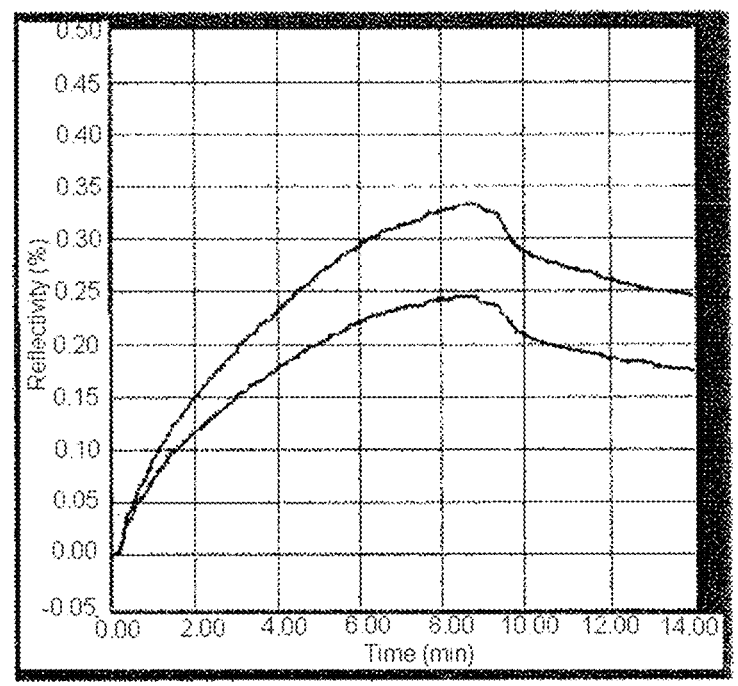
FIG. 2B provides results of a PEO-NHS biochip with anti-β-lactoglobulin antibody spots.
Figure 2C:
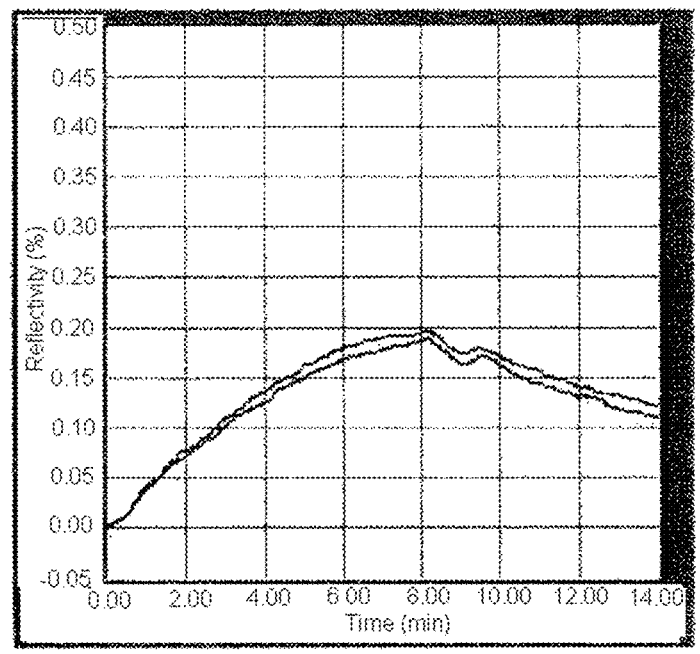
FIG. 2C provides results of a MUA-CDI biochip with MUA-CDI-functionalized surface.
Figure 2D:
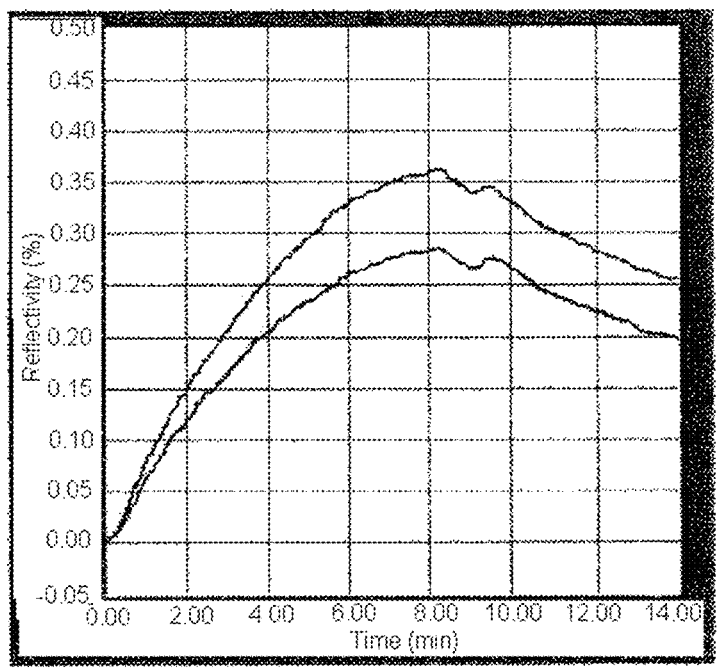
FIG. 2D provides results of a MUA CDI biochip with anti-β-lactoglobulin antibody spots.

In the case of the PEO-based chemistry proposed in the present invention, this adsorption of proteins on the zone not treated with the antibody is completely negligible (FIG. 2A) and does not require any adjustment during the quantification of proteins specifically adsorbed onto the antibody (FIG. 2B).

An MS analysis after an SPRi experiment according to the protocol described above on the PEO-NHS-functionalized and MUA-CDI-functionalized gold surfaces results in the detection of protein on the spots of antibody immobilized according to the two surface treatments. On the other hand, the MUA-CDI-functionalized surface devoid of antibody spots, which was inactivated by lysine treatment, results in the detection of protein by MALDI-MS. These results during the analysis by SPRi followed by a MALDI analysis illustrate the capacity of the MUA-CDI functionalization for creating nonspecific bonds which are detrimental to the analyses.

Example 5

In Situ Proteolytic Digestion During an SPR-MALDI-MS Analysis

Figure 5:
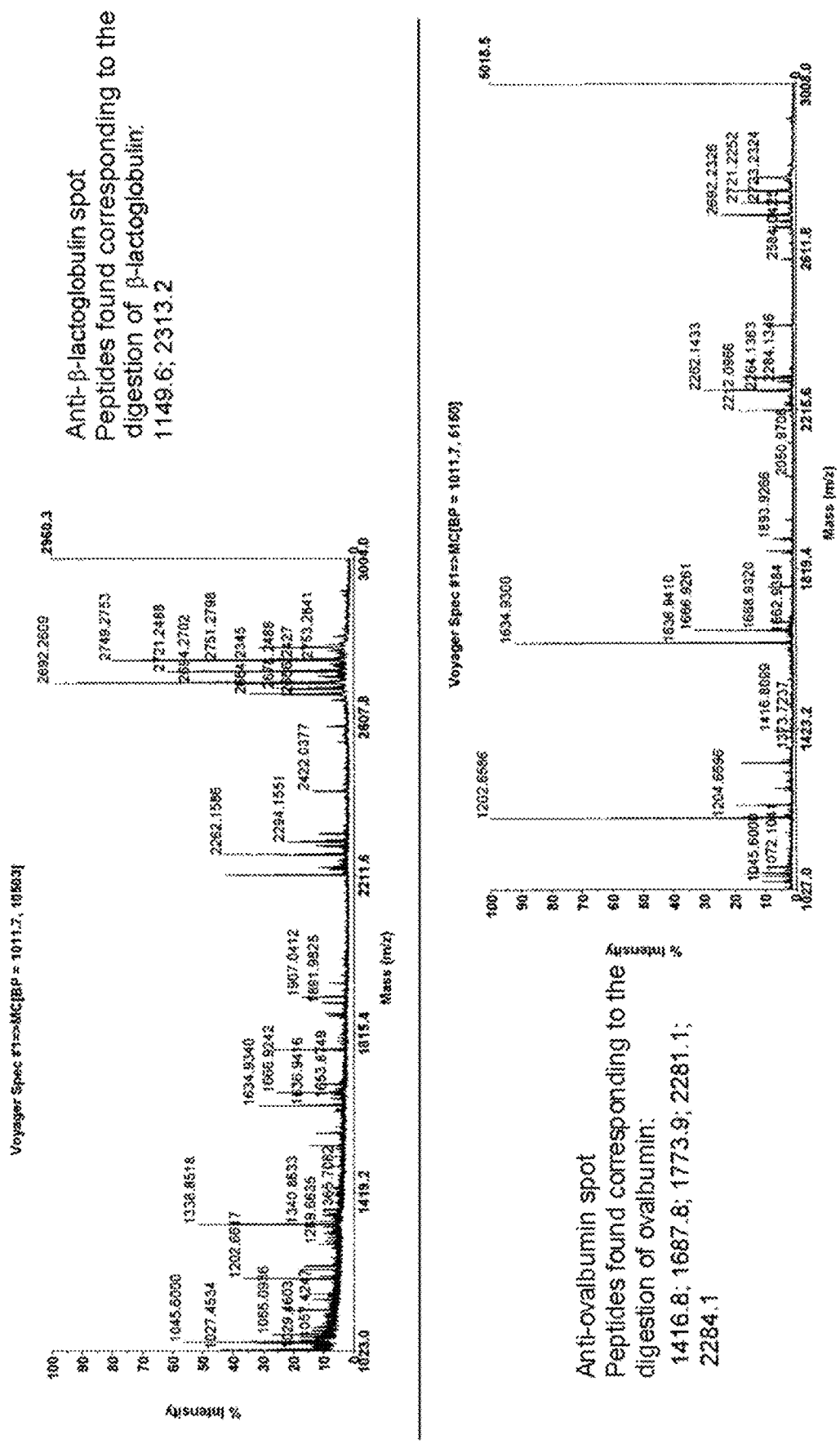
FIG. 5 represents an example of proteomic analysis after an SPRi experiment and then analysis by MALDI-TOF MS of the analytes digested in situ. The experiment is carried out on a biochip of the type PEO-NHS self-assembled monolayer on a gold surface.

Presentation of a Proteomic Analysis after an SPRi Experiment and Analysis by MALDI-TOF MS of the Analytes Digested In Situ, Said Experiment being Carried Out on a Biochip of the Type PEO-NHS Self-Assembled Monolayer at the Gold Surface This example relates to a tryptic digestion analyzed in-line by MALDI-TOF MS following the capture of the analyte by the immobilized antibody during the SPRi analysis on the functionalized support according to the invention (cf. FIG. 5).

This experiment relates to the ability to access proteomic data subsequent to an in-line SPRi-tryptic treatment—MALDI-MS coupling. This experiment concerns the interaction of ovalbumin and β-lactoglobulin on spots of anti-ovalbumin and anti-β-lactoglobulin antibodies deposited or immobilized on the functionalized surface.

The conditions of the experiment are the same as in example 2. The interaction of the ovalbumin and of the β-lactoglobulin with the anti-ovalbumin and anti-β-lactoglobulin antibodies (6 μM) immobilized on the surface is monitored by SPRi. For this (as in example 2), at the beginning of the experiment, lysine (100 μM) is injected in order to neutralize the NHS groups of the PEO-functionalized surface which have not reacted with the antibodies. Next, 500 μl of a mixture of the two proteins, ovalbumin and β-lactoglobulin, (50 μg/ml), is injected at the flow rate of 50 μl/min. The beginning of the injection of the mixture of proteins corresponds to the time t=0. Next, the functionalized support is rinsed for 10 min (t=8 min to t=18 min) with the 10 mM ammonium acetate running buffer, pH 7.5. Once the SPRi data have been recorded, the biochip is removed from the SPR instrument and then dried. The amounts retained are 40 pg/mm² of L-lactoglobulin on the anti-L-lactoglobulin spots and 48 pg/mm² of ovalbumin on the anti-ovalbumin spots. The proteolysis is carried out in situ by adding trypsin deposited on the antibody spots and incubating the chip for 1 h in a humid chamber at 37° C. The MALDI-TOF mass spectra are produced in reflectron mode (100 repeated shots and 500 accumulations; acceleration voltage 20 kV; voltage applied to the grid 68%; extraction delay 350 ns; laser intensity 2400). The chosen MALDI matrix is HCCA [L-cyano-4-hydroxycinnamic acid], at $10^{-1}$ M in 50/50 water/acetonitrile 0.1% TFA. The matrix is deposited onto the antibody spots. The mass spectra obtained show various signals, among which it is possible to identify those corresponding to the analyte digestion products.

Example 6

Identification of a Protein Captured on the SPRi Biochip, by In Situ Proteolytic Digestion and Sequencing by MALDI-MS/MS Tandem Mass Spectrometry This example is a presentation of a proteomic analysis by MALDI-MS and MALDI-MS/MS carried out after a SPRi experiment. The sequencing of peptides formed by the in situ proteolysis of a specifically retained protein makes it possible to unambiguously determine the identity thereof, the experiment being carried out on a biochip of the type PEO-NHS self-assembled monolayer at the gold surface.

This example therefore relates to the in-line sequencing of peptides by MALDI-MS/MS following the capture of a protein by the immobilized antibody during the SPRi analysis, and in situ tryptic digestion on the functionalized support according to the invention.

This experiment illustrates the possibility of identifying a protein specifically retained following an in-line SPRi-tryptic treatment—MALDI-MS and MALDI-MS/MS coupling. The example serving to illustrate the principle concerns the interaction between ovalbumin and the anti-ovalbumin antibody immobilized on the functionalized surface (cf. FIG. 6).

The immobilization of the anti-ovalbumin antibody on the surface (prepared according to example 1) and then the interaction of the ovalbumin with the anti-ovalbumin antibody is monitored by SPRi. The ovalbumin (200 μl, 100 μg/ml) is injected at the flow rate of 50 μl/min. Once the SPRi data have been recorded, the biochip is removed from the SPR instrument and then dried. The amount of ovalbumin retained is ~29 pg/mm² on the anti-ovalbumin antibody spots. The proteolysis is carried out in situ by depositing trypsin (0.5 μg/spot) and incubating the chip for 1 h at ambient temperature. The proteolysis reaction medium is maintained by adding, to the spots, twice 1 μl of 0.1 M ammonium acetate buffer, pH 8 (trypsin dilution buffer) every 20 minutes. MALDI-MS and MALDI-MS/MS mass spectra are then recorded from the surface of the same biochip (laser intensity 4900; acceleration voltage Source 1: 8 kV; collision cell 7 kV; Source 2: 15 kV). The chosen MALDI matrix is HCCA [L-cyano-4-hydroxycinnamic acid], at $10^{-1}$ M in 50/50 water/acetonitrile 0.1% TFA. The MALDI-MS mass spectra obtained show various signals, among which 9 peptides correspond to the ovalbumin digestion products (m/z 1345.73; 1555.72; 1571.71; 1581.72; 1597.71; 1687.83; 1773.89; 1858.96; 2008.94). Among these ions, the most abundant three were selected for MS/MS experiments (m/z 1555.7; 1687.8 and 1773.9). The fragment ions obtained from each of these peptides made it possible to identify, using the MASCOT software well known to those skilled in the art (http://www.matrixscience.com), the following peptide sequences:

```
m/z 1555.7:
                                    (SEQ ID NO: 2)
  AFKDEDTQAMPFR;

m/z 1687.8:
                                    (SEQ ID NO: 3)
  GGLEPINFQTAADQAR;
  and m/z 1773.9:
                                    (SEQ ID NO: 4)
  ISQAVHAAHAEINEAGR.
```

Figure 6A:
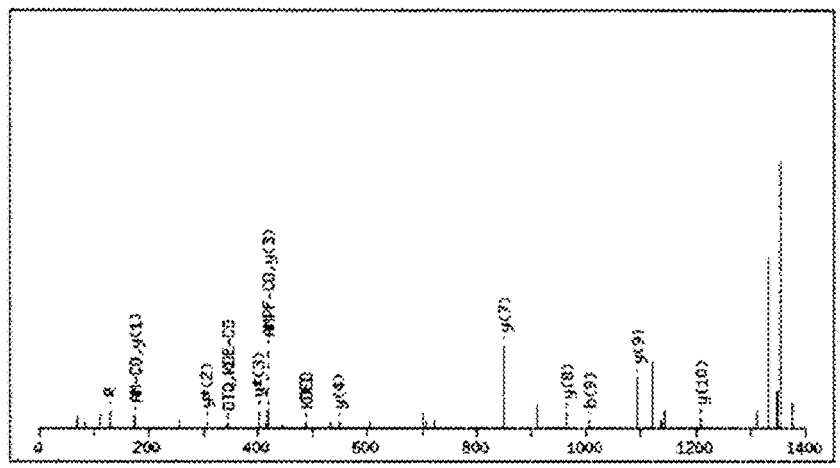
FIG. 6A with FIG. 6B represents an example of proteomic analysis after an SPRi experiment and then sequencing by MALDI-MS/MS of the peptides derived from the in situ digestion of the ovalbumin protein captured by the biochip. The experiment is carried out on a biochip of the PEO-NHS type self-assembled monolayer on a gold surface. The MALDI-MS/MS spectra of peptides derived from the digestion-on-biochip and the identification of the protein retained using the "Mascot" computer tool are represented on the figure.
Figure 6A:
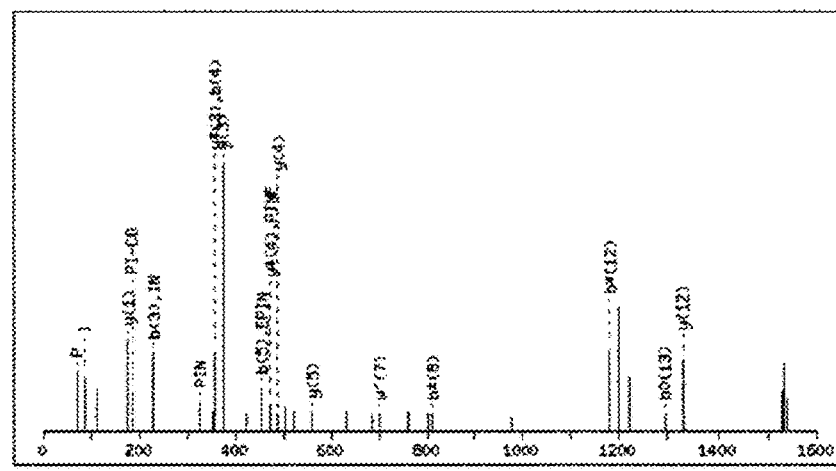
Figure 6A:
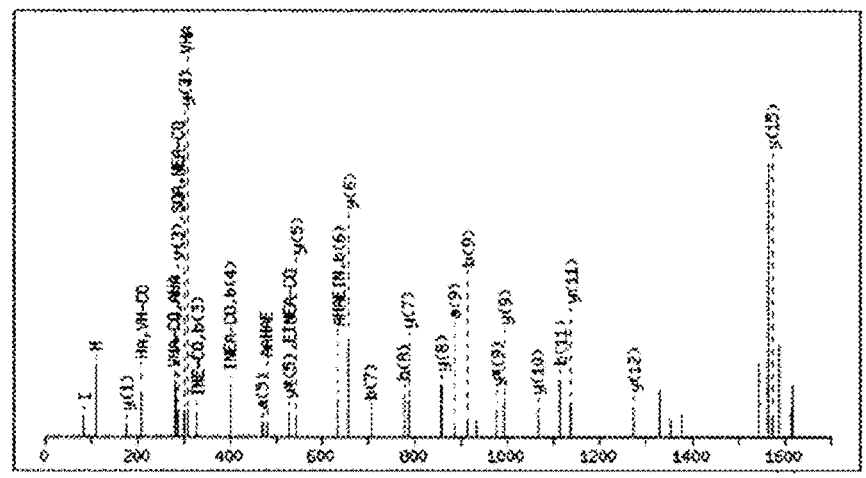

A data bank (SwissProt 56.2) search using the MASCOT software makes it possible to accurately identify, on the basis of these three peptide sequences, the protein specifically retained on the spots (cf. FIG. 6). The ovalbumin is identified unambiguously (Mowse score 145, sequence coverage 11%).

According to an identical approach, this SPRi-MALDI-MS/MS analysis was repeated with another protein, β-lactoglobulin, specifically retained by anti-β-lactoglobulin antibodies grafted onto the biochip, and then digested directly on the biochip. Eight peptides derived from the digestion were identified by MALDI-MS. On the basis of two of them (m/z 2313.27 and m/z 2707.3), MS/MS experiments followed by a data bank (SwissProt 56.2) search made it possible to identify the corresponding two peptide sequences (VYVEELKPTPEGDLEILLQK (SEQ ID NO:5) and VAGTWYSLAMAASDISLLDAQSAPLR (SEQ ID NO:6), respectively) and, consequently, the protein retained with a Mowse score of 120 (sequence coverage 25%).

We claim:

1. A method for functionalizing the metal face of a glass support for analysis by surface plasmon resonance, said method comprising grafting a self-assembled monolayer of poly(ethylene oxide) directly onto the metal face of said support,
   in which the metal of the metal face is gold, and
   in which the poly(ethylene oxide) is a compound of formula (I)

S—(CH$_2$)$_n$—(O—CH$_2$—CH$_2$)$_x$-D     (I)

in which:
   n is equal to 1 or 2;
   x is an integer between 5 and 16; and
   D is a group able to bind biomolecules or is a group that may be transformed in a group able to bind biomolecules.

2. The method according to claim 1, in which n is equal to 2.

3. The method according to claim 1, in which x is equal to 8.

4. The method according to claim 1, in which the PEO is O-(2-mercaptoethyl)-O'-(2-carboxyethy)heptaethylene glycol of formula HS—CH$_2$—CH$_2$—(O—CH$_2$—CH$_2$)$_8$—COOH.

5. The method according to claim 1, which method comprises the series of following steps:
   1) prior cleaning of the support;
   2) grafting of the PEO onto the support; and
   3) optionally, modification of group D of the PEO.

6. The method according to claim 5, in which the cleaning is carried out by UV-ozone treatment.

7. The method according to claim 5, in which group D represents a —COOH group which is modified in step 3) so as to give an N-hydroxysuccinimide group.

8. The method according to claim 5, in which the grafting is carried out by immersing the support in a vessel containing the poly(ethylene oxide) to be grafted, in solution.

9. A plasmon resonance, mass spectrometry support comprising
a glass support, said glass support comprising a single, functionalized face, said face comprising a gold, surface plasmon resonance measuring surface, said measuring surface comprising a self-assembled monolayer of poly(ethylene oxide) directly grafted to the gold,
the poly(ethylene oxide) being a compound of formula (I)

$$—S(CH_2)_n—(O—CH_2—CH_2)_x-D \qquad (I)$$

in which:
n is equal to 1 or 2;
x is an integer between 5 and 16; and
D is a group able to bind biomolecules or is a group that may be transformed in a group able to bind biomolecules.

10. The plasmon resonance, mass spectrometry support according to claim 9, further comprising biomolecules immobilized on said support via the D group.

11. A method of surface plasmon resonance comprising binding molecules to be detected by plasmon resonance to a functionalized support according to claim 9.

12. The method according to claim 11, said method comprising studying the molecular interactions of the molecules by surface plasmon resonance.

13. A method of mass spectrometry comprising structurally identifying molecules covalently linked to the support according to claim 9.

14. The method according to claim 13, in which the mass spectrometry is carried out with MALDI-type ionization.

15. The method consecutively performing surface plasmon resonance and mass spectrometry on a sample comprising immobilizing molecules on the support of claim 9;
analyzing said molecules on the support by surface plasmon resonance and then
analyzing said molecules on the support by mass spectrometry.

16. The method according to claim 15, in which analysis by surface plasmon resonance is an analysis by surface plasmon resonance i.

17. The method according to claim 15, in which the analysis by mass spectrometry is an analysis of MALDI.

18. A method for coupling an analysis by surface plasmon resonance (SPR) with an analysis by mass spectrometry comprising:
1) immobilization of one or more molecules on the support according to claim 9; then
2) placing of the support in an SPR analyzer and analyzing, by SPR, of the interactions between the one or more molecules immobilized and a sample of analytes; then
3) removing the support from the SPR analyzer and placing the support in a mass spectrometer, and performing structural analysis, by MS, of the analytes specifically retained by the one or more molecules during the SPR analysis.

19. A method for coupling an analysis by SPR with an analysis by MS comprising:
1) immobilizing one or more molecules on a support according to claim 9; then
2) placing of the support in an SPR analyzer and analyzing by SPR the interactions between the one or more molecules immobilized and a sample of analytes;
3) in situ localized enzyme digestion of the analytes retained on the one or more molecules immobilized on the support, then placing of the support in a mass spectrometer structurally analyzing, by MS the products of digestion of the analyte(s) present on the support.

20. A method for coupling an analysis by SPR with an analysis by MS comprising:
1) immobilization of one or more molecules on the support according to claim 9; then
2) placing of the support in an SPR analyzer and analyzing, by SPR, of the interactions between the one or more molecules immobilized and a sample of analytes; then
3) removal of the support from the SPR analyzer and placing of said support in a mass spectrometer, and structurally analyzing, by MS, the analytes specifically retained by the molecules during the SPR analysis; then
4) in situ localized enzyme digestion of the analytes retained on the molecules immobilized on the support, and placing of the support in a mass spectrometer, and structurally analyzing, by MALDI MS or MALDI MS/MS, the products of digestion of the molecules present on the support.

21. The plasmon resonance, mass spectrometry support of claim 9, wherein D is an N-hydroxysuccinimide group, a succinimidyl ester group, a sulfosuccinimidyl ester group, a maleimide functionalized group, an iodoacetyl functionalized group, or a carboxylic acid group.

* * * * *

SEQUENCE LISTING

```
<160> NUMBER OF SEQ ID NOS: 6

<210> SEQ ID NO 1
<211> LENGTH: 386
<212> TYPE: PRT
<213> ORGANISM: Gallus gallus

<400> SEQUENCE: 1

Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
```

```
            20                  25                  30
Ile Ala Ile Met Ser Ala Leu Ala Met Val Tyr Leu Gly Ala Lys Asp
            35                  40                  45
Ser Thr Arg Thr Gln Ile Asn Lys Val Val Arg Phe Asp Lys Leu Pro
 50                  55                  60
Gly Phe Gly Asp Ser Ile Glu Ala Gln Cys Gly Thr Ser Val Asn Val
 65                  70                  75                  80
His Ser Ser Leu Arg Asp Ile Leu Asn Gln Ile Thr Lys Pro Asn Asp
                    85                  90                  95
Val Tyr Ser Phe Ser Leu Ala Ser Arg Leu Tyr Ala Glu Glu Arg Tyr
                100                 105                 110
Pro Ile Leu Pro Glu Tyr Leu Gln Cys Val Lys Glu Leu Tyr Arg Gly
                115                 120                 125
Gly Leu Glu Pro Ile Asn Phe Gln Thr Ala Ala Asp Gln Ala Arg Glu
                130                 135                 140
Leu Ile Asn Ser Trp Val Glu Ser Gln Thr Asn Gly Ile Ile Arg Asn
145                 150                 155                 160
Val Leu Gln Pro Ser Ser Val Asp Ser Gln Thr Ala Met Val Leu Val
                165                 170                 175
Asn Ala Ile Val Phe Lys Gly Leu Trp Glu Lys Ala Phe Lys Asp Glu
                180                 185                 190
Asp Thr Gln Ala Met Pro Phe Arg Val Thr Glu Gln Glu Ser Lys Pro
                195                 200                 205
Val Gln Met Met Tyr Gln Ile Gly Leu Phe Arg Val Ala Ser Met Ala
                210                 215                 220
Ser Glu Lys Met Lys Ile Leu Glu Leu Pro Phe Ala Ser Gly Thr Met
225                 230                 235                 240
Ser Met Leu Val Leu Leu Pro Asp Glu Val Ser Gly Leu Glu Gln Leu
                245                 250                 255
Glu Ser Ile Ile Asn Phe Glu Lys Leu Thr Glu Trp Thr Ser Ser Asn
                260                 265                 270
Val Met Glu Glu Arg Lys Ile Lys Val Tyr Leu Pro Arg Met Lys Met
                275                 280                 285
Glu Glu Lys Tyr Asn Leu Thr Ser Val Leu Met Ala Met Gly Ile Thr
                290                 295                 300
Asp Val Phe Ser Ser Ser Ala Asn Leu Ser Gly Ile Ser Ser Ala Glu
305                 310                 315                 320
Ser Leu Lys Ile Ser Gln Ala Val His Ala Ala His Ala Glu Ile Asn
                325                 330                 335
Glu Ala Gly Arg Glu Val Val Gly Ser Ala Glu Ala Gly Val Asp Ala
                340                 345                 350
Ala Ser Val Ser Glu Glu Phe Arg Ala Asp His Pro Phe Leu Phe Cys
                355                 360                 365
Ile Lys His Ile Ala Thr Asn Ala Val Leu Phe Phe Gly Arg Cys Val
                370                 375                 380
Ser Pro
385

<210> SEQ ID NO 2
<211> LENGTH: 13
<212> TYPE: PRT
<213> ORGANISM: Gallus gallus

<400> SEQUENCE: 2
```

```
Ala Phe Lys Asp Glu Asp Thr Gln Ala Met Pro Phe Arg
1               5                   10
```

<210> SEQ ID NO 3
<211> LENGTH: 16
<212> TYPE: PRT
<213> ORGANISM: Gallus gallus

<400> SEQUENCE: 3

```
Gly Gly Leu Glu Pro Ile Asn Phe Gln Thr Ala Ala Asp Gln Ala Arg
1               5                   10                  15
```

<210> SEQ ID NO 4
<211> LENGTH: 17
<212> TYPE: PRT
<213> ORGANISM: Gallus gallus

<400> SEQUENCE: 4

```
Ile Ser Gln Ala Val His Ala Ala His Ala Glu Ile Asn Glu Ala Gly
1               5                   10                  15

Arg
```

<210> SEQ ID NO 5
<211> LENGTH: 20
<212> TYPE: PRT
<213> ORGANISM: Bos taurus

<400> SEQUENCE: 5

```
Val Tyr Val Glu Glu Leu Lys Pro Thr Pro Glu Gly Asp Leu Glu Ile
1               5                   10                  15

Leu Leu Gln Lys
                20
```

<210> SEQ ID NO 6
<211> LENGTH: 26
<212> TYPE: PRT
<213> ORGANISM: Bos taurus

<400> SEQUENCE: 6

```
Val Ala Gly Thr Trp Tyr Ser Leu Ala Met Ala Ala Ser Asp Ile Ser
1               5                   10                  15

Leu Leu Asp Ala Gln Ser Ala Pro Leu Arg
                20                  25
```